United States Patent [19]

Manning

[11] Patent Number: 4,537,616
[45] Date of Patent: Aug. 27, 1985

[54] HERBICIDAL 2,6-DIOXOCYCLOHEXYLIDENE DERIVATIVES

[75] Inventor: David T. Manning, Raleigh, N.C.

[73] Assignee: Union Carbide Corporation, Danbury, Conn.

[21] Appl. No.: 509,456

[22] Filed: Jun. 30, 1983

[51] Int. Cl.³ .................. A01N 43/02; C07D 239/02; C07D 233/00; C07D 243/04
[52] U.S. Cl. .................................. 71/92; 260/239 B; 544/335; 548/300
[58] Field of Search ........................... 544/335; 71/92; 260/239 B; 548/300

[56] References Cited

FOREIGN PATENT DOCUMENTS 11097 4/1973 Japan .

OTHER PUBLICATIONS

Chem. Pharm. Bull 25 (10) 2775–2778 (1977), Teruaki Tsujikawa et al.
Heterocycles, vol. 6, No. 3, 1977, Teruaki Tsujikawa et al.
David Black, 1976, (pp. 1944–1950), J.C.S. Perkin 1 (1976) (18).
Hans Jurek et al., 2–(1,3–Dioxo-2–Indanyliden)Benzimidazolin ein Indigo Isomers, pp. 2276–2282.
Chem. Abst. 83-206076b, Hatada et al., equi Yak. Zassh. 95, 623 (1975).
Francesco Paolo Colonna et al., J.C.S. Perkin II (1978) (4) 279–283.
J. Sandstrom et al., Studies of Polarized Ethylenes-VIII.
Kishida, equiv. Japan 73, 11097, Chem. Abst. vol. 79 (1973) 32037q.
U. Sjostrand et al., Tetrahedron 34 (22) 3305 (1978).
Koichi et al., Chem. Pharm. Bull 20 (i) 97–101 (1971).
J. P. Célérier, Tetratron Letters 22 (10) 963 (1981).
J. P. Célérier, Synthesis (1981) (2) 130–133.
J. P. Célérier, J. Org. Chem. 44; 3089 (1979).
P. Kaproa et al., Tet. Letters (24) 2255 (1981).
Washawsky et al., J. Het. Chem. 7 (4) 917 (1970).
Chem. Abst. vol. 85, 1976, 85:20763j.
Iwataki, Isao et al., Chem. Abst. 91:157346u (1979).
Nippon Soda Co. Chem. Abst. 93:162729s (1980).
Nippon Soda Co. Chem. Abst. 94:11639g (1981).

Primary Examiner—Donald G. Daus
Assistant Examiner—Cecilia Shen
Attorney, Agent, or Firm—Clement J. Vicari

[57] ABSTRACT

This invention relates to certain 2,6-dioxocyclohexylidene-substituted heterocyclic compounds which show broad-spectrum herbicidal activity against a variety of broadleaf and grassy weeds.

12 Claims, No Drawings

HERBICIDAL 2,6-DIOXOCYCLOHEXYLIDENE DERIVATIVES

BACKGROUND OF THE INVENTION

1. Field of the Invention

This invention relates to certain 2,6-dioxocyclohexylidene derivatives. In one aspect, the invention relates to novel compositions which exhibit herbicidal activity against a variety of broadleaf and grassy weeds. In another aspect, the invention relates to a method of controlling undesirable plant growth, by applying a herbicidally effective amount of said compositions to the plants. In a further aspect of the invention, certain of the compositions show cotton defoliant activity.

2. Description of the Prior Art

The present invention relating to the 2,6-dioxocyclohexylidene derivatives and their herbicidal activity originated during an investigation which is described in U.S. Ser. No. 288,335 filed July 30, 1981. This prior investigation relates to certain herbicidal 2-(2-pyridinyl)-1,3-cyclohexanediones typified by the following:

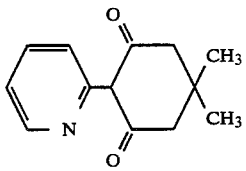

The compounds of this invention differ from the above described pyridinyl diones in having non-aromatic rings attached to the 1,3-cyclohexanedione 2-position by a double bond.

Furthermore, prior to the present invention, certain structures included within the scope of this invention had been investigated for their antihypertensive properties. For example, T. Tsujikawa et al., in Heterocycles 6 (3) 261–266 (1977) and Chem. Pharm. Bull. 25 2775 (1977), reported certain 2-(2-pyrrolidinylidene)-; 2-(2-piperidinylidene)-; and 2-(hexahydro-2H-azepin-2-ylidene)-1,3-cyclohexanediones and their derivatives.

In addition, T. Hatada et al in Yakugaku Zasshi. 95 623 (1975) reported certain 2-(2-imidazolidinylidene)-1,3-cyclohexanedione structures, albeit herbicidal use was not disclosed.

The closest prior art compound structurally with known herbicidal activity to the compounds of this invention is the following disclosed in Japanese Patent 11,097 patented Apr. 10, 1973 (Chem. Abst. 79 32037g (1973)):

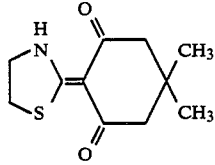

which differs from all of the subject compounds by the presence of a sulfur atom in the heterocyclic (thiazolidine) ring.

SUMMARY OF THE INVENTION

This invention relates to certain 2,6-dioxocyclohexylidene-substituted heterocyclic compounds which show broad-spectrum herbicidal activity against a variety of broadleaf and grassy weeds. Furthermore, although the compounds of this invention are safe for use on several crops, certain of the compounds of this invention show cotton defoliant activity.

DETAILED DESCRIPTION OF THE INVENTION

In its broad aspect, this invention relates to certain novel compounds, novel herbicidal compositions and their various uses.

The novel compounds of this invention can be conveniently represented by the following formula:

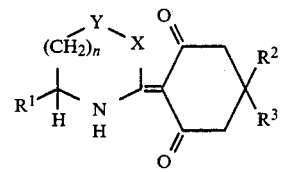

wherein:

X is $CH_2$ or NH;

Y is $CH_2$, $CHR^4$ or O wherein $R^4$ is $C_1$–$C_3$ alkyl and with the proviso that when Y is O, X is $CH_2$;

$R^1$ is hydrogen or $C_1$–$C_3$ alkyl, with the proviso that the number of carbon atoms in $R^1$ plus Y is $\leq 5$;

$R^2$ is hydrogen or $C_1$–$C_5$ straight chain, branched or cyclic alkyl;

$R^3$ is $C_1$–$C_3$ straight chain alkyl or $R^2$ and $R^3$ together may form a cyclopentane or cyclohexane ring wherein the number of carbon atoms in $R^2$ plus $R^3$ is $\leq 6$; and n is 0, 1 or 2;

with the proviso that when $R^2$ and $R^3$ are $CH_3$ (a) and $R^1$ is H, Y and X cannot both be $CH_2$; and (b) when Y is $CH_2$ and n is O. X cannot be NH; and (c) when X and Y are both $CH_2$ and n is O, $R^1$ cannot be n-$C_3H_7$.

The compounds of the subject invention are non-enolic, i.e. they are not in equilibrium with the unsaturated ring tautomers.

The novel herbicidal compositions of this invention comprise an acceptable carrier and an active toxicant wherein said toxicant comprises a herbicidally effective amount of a compound of the following generic formula:

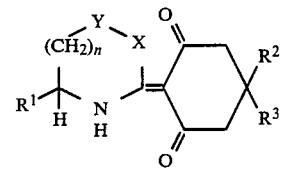

wherein:

X is $CH_2$ or NH;

Y is $CH_2$, $CHR^4$ or O wherein $R^4$ is $C_1$–$C_3$ alkyl and with the proviso that when Y is O, X is $CH_2$;

$R^1$ is hydrogen or $C_1$–$C_3$ alkyl, with the proviso that the number of carbon atoms in $R^1$ plus Y is $\leq 5$;

$R^2$ is hydrogen or $C_1$–$C_5$ straight chain, branched or cyclic alkyl;

$R^3$ is $C_1$–$C_3$ straight chain alkyl or $R^2$ and $R^3$ together may form a cyclopentane or cyclohexane ring wherein the number of carbon atoms in $R^2$ plus $R^3$ is $\leq 6$; and n is 0, 1 or 2;

The preferred compounds of this invention are those wherein:

Y is $CH_2$, $CHR^4$ or O wherein $R^4$ is $C_1$-$C_3$ alkyl;

the total number of carbon atoms in $R^2$ and $R^3$ together are equal to or less than 4; and n is 0 or 1, with the proviso that when Y is O, X is $CH_2$ and n is 1.

The most preferred compounds of this invention are those wherein:

Y is $CHR^4$ wherein $R^4$ is $CH_3$ or $C_2H_5$; the total number of carbon atoms in $R^2$ and $R^3$ together are 2 or 3; and n is 1.

Illustrative of the novel compounds of this invention include, among others:

5-(1-Methylethyl)-2-(4-methyl-2-piperidinylidene)-1,3-cyclohexanedione
2-(4-Ethyl-2-piperidinylidene)-5-(1-methylethyl)-1,3-cyclohexanedione
2-(4-Methyl-2-piperidinylidene)-5-(1-methylpropyl)-1,3-cyclohexanedione
5,5-Dimethyl-2-(4-ethyl-2-piperidinylidene)-1,3-cyclohexanedione
5-Ethyl-2-(4-ethyl-2-piperidinylidene)-1,3-cyclohexanedione
5-(1-Methylpropyl)-2-(2-pyrrolidinylidene)-1,3-cyclohexanedione
5-Methyl-5-(1-methylethyl)-2-(2-piperidinylidene)-1,3-cyclohexanedione
5-Methyl-2-(4-methyl-2-piperidinylidene)-5-(1-methylethyl)-1,3-cyclohexanedione
5-Methyl-5-(1-methylethyl)-2-(2-pyrrolidinylidene)-1,3-cyclohexanedione
2-(4-Methyl-2-hexahydropyrimidinylidene)-5-(1-methylpropyl)-1,3-cyclohexanedione
5,5-Dimethyl-2-(4-ethyl-2-hexahydropyrimidinylidene)-1,3-cyclohexanedione
2-(4-Ethyl-2-hexahydropyrimidinylidene)-5-(1-methylethyl)-1,3-cyclohexanedione
2-(2-Imidazolidinylidene)-5-(1-methylpropyl)-1,3-cyclohexanedione
2-(2-Imidazolidinylidene)-5-methyl-5-(1-methylethyl)-1,3-cyclohexanedione
2-(2-Hexahydropyrimidinylidene)-5-methyl-5-(1-methylethyl)-1,3-cyclohexanedione
5-Methyl-5-(1-methylethyl)-2-(4-methyl-2-hexahydropyrimidinylidene)-1,3-cyclohexanedione
2-(4,6-Dimethyl-2-hexahydropyrimidinylidene)-5-(1-methylethyl)-1,3-cyclohexanedione
5-(1-Methylethyl)-2-(3-morpholinylidene)-1,3-cyclohexanedione
5,5-Dimethyl-2-(4,6-dimethylpiperidinylidene)-1,3-cyclohexanedione
2-(4,6-Dimethylpiperidinylidene)-5-(1-methylethyl)-1,3-cyclohexanedione
5,5-Dimethyl-2-(4-methyl-2-pyrrolidinylidene)-1,3-cyclohexanedione
5,5-Dimethyl-2-(5-methyl-2-pyrrolidinylidene)-1,3-cyclohexanedione
5-(1,1-Dimethylethyl)-2-(2-piperidinylidene)-1,3-cyclohexanedione
5-(1-Ethylpropyl)-2-(2-piperidinylidene)-1,3-cyclohexanedione
9-(2-Piperidinylidene)-spiro[5.5]undecane-8,10-dione Illustrative of known compounds from which the novel herbicidal compositions of this invention can be prepared include, among others:

5,5-Dimethyl-2-(2-pyrrolidinylidene)-1,3-cyclohexanedione
5,5-Dimethyl-2-(2-piperidinylidene)-1,3-cyclohexanedione
5,5-Dimethyl-2-(hexahydro-2H-azepin-2-ylidene)-1,3-cyclohexanedione
5,5-Dimethyl-2-(2-imidazolidinylidene)-1,3-cyclohexanedione The preferred compounds of this invention include the following:

5,5-Dimethyl-2-(4-methyl-2-piperidinylidene)-1,3-cyclohexanedione
5-(1-Methylethyl)-2-(2-piperidinylidene)-1,3-cyclohexanedione
5-(1-Methylethyl)-2-(2-pyrrolidinylidene)-1,3-cyclohexanedione
5,5-Dimethyl-2-(6-methyl-2-piperidinylidene)-1,3-cyclohexanedione
5-(1-Methylethyl)-2-(2-imidazolidinylidene)-1,3-cyclohexanedione
5,5-Dimethyl-2-(2-hexahydropyrimidinylidene)-1,3-cyclohexanedione
5-(1-Methylethyl)-2-(2-hexahydropyrimidinylidene)-1,3-cyclohexanedione
5,5-Dimethyl-2-(4-methyl-2-hexahydropyrimidinylidene)-1,3-cyclohexanedione
5-(1-Methylethyl)-2-(4-methyl-2-hexahydropyrimidinylidene)-1,3-cyclohexanedione
5,5-Dimethyl-2-(3-morpholinylidene)-1,3-cyclohexanedione In practice, two general methods were used to prepare the 2,6-dioxocycloalkylideneamines of this invention.

The first general procedure which was employed for most of the compounds was taught by Tsujikawa et al, supra using lactim ethers as follows:

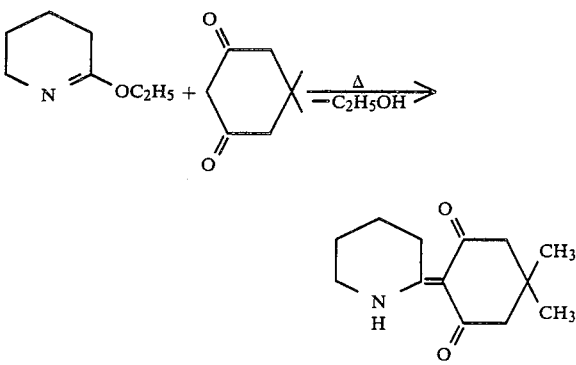

This procedure is also applicable to 5-membered ring lactim ethers.

The preferred conditions for the condensation reactions involving the lactim ethers are as follows:

(a) The reactions can be conducted solventless or in ethanol, n-propanol, isopropyl alcohol, higher alcohols, toluene, and dioxane; although with 5 membered ring compounds, isopropyl alcohol is the most preferred solvent. With 6 and 7 membered ring lactims, it is most preferred to run the reaction without a solvent.

(b) The temperature of the reaction can be from about 60°–150° C. at from about 0.5 to 8 hours however, the most preferred reaction temperature range is from about 80°–130° C. at from about 2 to 4 hours.

(c) No catalyst is required for the lactim ether reactions and although the lactim ether to 1,3-dione ratio can vary widely, the most preferred ratio range is from about 1:1 to about 1:1.5. Use of excess 1,3-dione may be desirable when reactions with relatively high cost lactim ethers are involved since essentially complete conversion of the latter can thus be achieved and unreacted 1,3-dione is removed from the product by extraction with an aqueous base.

The second general procedure which was used to prepare several of the compounds is taught by Hirai et al., Chem Pharm. Bull 20 (1), 97 (1972) and is as follows:

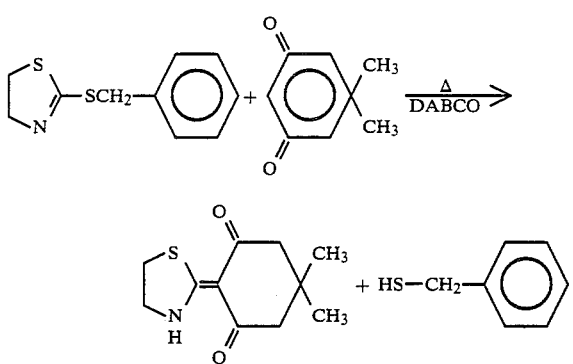

This procedure is also employed with thioethers of dinitrogen heterocycles wherein the starting reactant can be

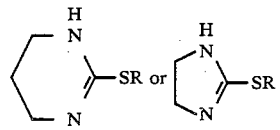

where R can be a lower alkyl or benzyl group.

The preferred conditions for the condensation reactions involving the lactim thioethers are as follows:

(a) It is most preferred that the reactions be conducted solventless however dioxane, toluene and xylenes can be used, (b) The temperature of the reactions can be from about 80°–150° C. at from about 2 to 12 hours, however, the most preferred reaction temperature range is from about 100°–130° C. and from about 5 to 8 hours.

(c) The reactant ratios are similar to those disclosed above for the lactim ethers.

(d) With lactim thioethers, it is preferred to conduct the condensation reactions in the presence of at least one of the following catalysts:

1,4-Diazabicyclo[2.2.2]octane (DABCO) (most preferred);
1,5-diazabicyclo[4.3.0]non-5-ene;
1,8-diazabicyclo[5.4.0]undec-7-ene;
4-diethylaminopyridine;
4-dimethylaminopyridine; triethyl amine; and trimethylamine.

Lactim ethers can be prepared by the method of Oishi et al, Chem. Pharm. Bull. 17 2306 (1969) from appropriate lactims by reaction with Meerwein's reagent.

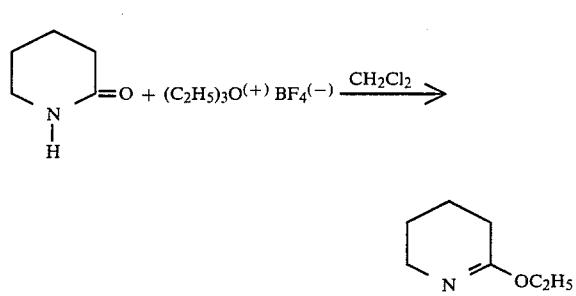

Thioethers of dinitrogen heterocycles can be prepared by the procedures of Lloyd and Millar, Tetrahedron 36 (18), 2675 (1980) in which the appropriate cyclic thiourea is reacted with benzyl bromide and the resulting hydrobromide salt is then treated with sodium hydroxide, as follows:

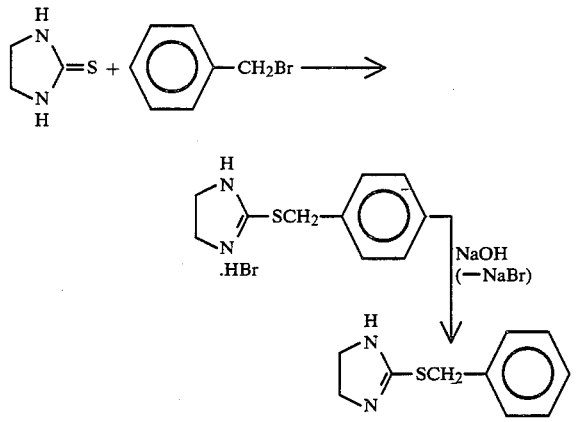

Other thioethers are also suitable for the desired condensation, such as:

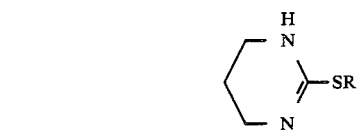

(R = $CH_3$, $C_2H_5$, i-$C_3H_7$, other alkyl)

A number of starting materials can be prepared by various prior art disclosures as set forth below. 3-Ethoxy-3,4-dihydromorpholine is prepared from 3-morpholinone by the general procedure of U.S. Pat. No. 3,973,017, Example 2 using the method of Oishi et al, supra. 5-(1-Methylethyl)-1,3-cyclohexanedione is synthesized from 5-methyl-3-hexen-2-one and diethyl malonate according to the procedure of Shriner and Todd, Org. Syn. Coll. Vol. II, page 200 for preparing dimedone. 2-Ethoxy-6-methyl-3,4,5,6-tetrahydropyridine is prepared by reacting 6-methyl-2-piperidone with triethyloxonium tetrafluoroborate according to the method of Oishi et al., supra. 2-Ethoxy-4-methyl-3,4,5,6-tetrahydropyridine is similarly prepared (Oishi et al) from 4-methyl-2-piperidone. The latter is synthesized by liquid-phase ammonolysis of 4-methyltetrahydro-2H-pyran- 2-one under conditions similar to that disclosed in Belgium Pat. No. 660,505 (Chem. Abs. 64 1957e). The 4-methyltetrahydro-2H-pyran-2-one is prepared by sodium borohydride reduction of 4-methylglutaric anhydride using procedure of Takano and Ogasawara, Synthesis (1974), 42–43. Tetrahydro-4-methyl-2(1H)-pyrimidenethione, the precursor of 1,4,5,6-tetrahydro-2-(benzylthio)-4(or 6)-methylpyrimidine (above) is prepared by reaction of butane-1,3-diamine (Campbell et al, Inorg. Chem. 12 1836 (1973)) with carbon disulfide according to the procedure of Allen et al., Org. Syn. Coll. Vol. III, page 394.

The following examples illustrate the best mode presently contemplated for the preparation of the compounds of this invention.

EXAMPLE 1

Compound No. 8

5,5-Dimethyl-2-(6-methyl-2-piperidinylidene)-1,3-cyclohexanedione

2-Ethoxy-6-methyl-3,4,5,6-tetrahydropyridine (14.12 grams, 0.1 mole) and dimedone (14.02 grams, 0.1 mole) are charged to a flask and heated, with stirring, at 120°–122° C. for a 3.7-hour period. The solid residue is dissolved in methylene chloride and that solution extracted three times with 3N NaOH to remove unreacted dimedone. The methylene chloride layer is extracted four times with 3N HCl and the aqueous acid layer adjusted for pH 7 which will cause separation of 1.72 grams of nearly pure product as an oil which is recovered as a yellow crystalline solid upon methylene chloride extraction and stripping. Evaporation of the original methylene chloride phase, following acid extraction, gives the remaining product as a yellow solid. The latter dissolved in ethyl ether and extracted with 3N NaOH, the ether layer dried, filtered and stripped and the residue recrystallized from cyclohexane gives 11.21 grams of pure product, m.p. 94.5°–96° C. The total yield of pure fractions is 55.0%.

EXAMPLE 2

Compound No. 1

5,5-Dimethyl-2-(4-methyl-2-piperidinylidene)-1,3-cyclohexanedione

A mixture of 2-ethoxy-4-methyl-3,4,5,6-tetrahydropyridine (9.27 grams, 0.066 mole) and dimedone (9.20 grams, 0.066 mole) is heated at 112°–113° C. for a 3-hour period. The cooled residue is dissolved in ethyl ether and extracted with three portions of 3N HCl. A solution of 6N sodium hydroxide is added to the strongly acidic solution causing the product to separate as a white solid, with precipitation complete at a final pH of 1. The crude product weighs 4.32 grams on drying and melts at 172°–175° C. Recrystallization from a large volume of cyclohexane gives 2.64 grams of pure material, m.p. 174° C.

EXAMPLE 3

Compound No. 7

5-(1-Methylethyl)-2-(2-pyrrolidinylidene)-1,3-cyclohexanedione

A mixture of 2-ethoxy-1-pyrroline (9.05 grams, 0.08 mole), and 5-(1-methylethyl)-1,3-cyclohexanedione (12.34 grams, 0.08 mole), in 50 mL of isopropyl alcohol solvent is heated under reflux for 2 hours. After standing overnight, the cooled reaction solution will deposit white, crystalline product which is collected, washed with cold solvent and dried to give 2.2 grams of solid, m.p. 143°–145° C. The filtrate is evaporated and the residue dissolved in dichloromethane and the solution extracted with three portions of 3N NaOH followed by three portions of 3N hydrochloric acid. Addition of 3N NaOH to the acid solution causes precipitation of an 0.87-gram portion of product, m.p. 143.5°–145° C. The latter is recrystallized from ethyl acetate for an analytical sample.

EXAMPLE 4

Compound No. 10

5-(1-Methylethyl)-2-(2-imidazolidinylidene)-1,3-cyclohexanedione

A mixture of 2-benzylthio-4,5-dihydro-1H-imidazole (15.4 grams, 0.08 mole), 5-(1-methylethyl)-1,3-cyclohexanedione (12.3 grams, 0.08 mole) and 0.11 gram of DABCO is heated at 115°–120° C., with stirring, for a period of 7.1 hours. The cooled residue is dissolved in dichloromethane and the solution extracted with three portions of 3N sodium hydroxide, then with four portions of 3N hydrochloric acid. The organic phase is then dried over magnesium sulfate and evaporated, to give 15.31 grams of crude product as a yellow solid. The material is recrystallized twice from toluene and once from ethyl acetate, to give 2.58 grams of product, m.p. 223°–225° C.

EXAMPLE 5

Compound No. 11

5.5-Dimethyl-2-(2-hexahydropyrimidinylidene)-1,3-cyclohexanedione

A mixture of 2-benzylthio-3,4,5,6-tetrahydropyrimidine (7.77 grams, 0.038 mole) and dimedone (5.28 grams, 0.038 mole) is stirred and heated with 0.05 gram of DABCO at 111°–112° C. for a 7-hour period. The reaction mixture is dissolved in methylene chloride and extracted with 3 portions of 3N sodium hydroxide. The methylene chloride solution is then extracted with 3N HCl and the latter extract made strongly basic causing precipitation of 0.49 gram of pure product, m.p. 197°–199° C.

The methylene chloride phase is evaporated giving a solid which is stirred with 3N HCl and ether, removing an acid-insoluble oil. The aqueous acid layer is adjusted to pH 12, causing a solid to precipitate which is filtered off, water washed and dried. Readjusting the pH of the filtrate to 12 produces additional precipitate giving a total, after drying, of 4.77 grams of pure product, melting in the range of 194°–197° C. The total yield is 62.9%.

EXAMPLE 6

Compound No. 14

5,5-Dimethyl-2-(4-methyl-2-hexahydropyrimidinylidene)-1,3-cyclohexanedione

A mixture of 1,4,5,6-tetrahydro-2-(benzylthio)-4(or 6)-methylpyrimidine (10.9 grams, 0.05 mole), dimedone (6.93 grams 0.05 mole) and 70 mg of DABCO is heated at 110°–112° C., with stirring, for a period of 5.13 hours. The cooled solidifed residue is dissolved in methylene chloride and the resulting solution extracted three times with 3N NaOH to remove unreacted dimedone. The organic phase is then extracted three times with 3N HCl, and the combined aqueous acid extracts are then neutralized with 3N NaOH causing the product to precipitate as a pale yellow solid, which weighs, after drying, 5.95 grams (56.4% yield), and melts at 164°–165° C. Recrystallization from ethyl acetate gives an analytical sample, m.p. 165°–166° C.

EXAMPLE 7

Compound No. 13

5-(1-Methylethyl)-2-(4-methyl-2-hexahydropyrimidinylidene)-1,3-cyclohexanedione

A mixture of 1,4,5,6-tetrahydro-2-(benzylthio)-4(or 6)-methylpyrimidine (15.42 grams, 0.07 mole), 5-(1-methylethyl)-1,3-cyclohexanedione (10.8 grams, 0.07 mole) and 0.1 gram of DABCO is stirred and heated at 105°–110° C. for a period of 5.92 hours. The cooled residue is dissolved in methylene chloride and extracted with three portions of 3N sodium hydroxide followed by three extractions with 6N hydrochloric acid. The pH of the combined acid extracts is adjusted to 12 causing precipitation of an oil, which is extracted with ether to give, after evaporation, 5.13 grams of a yellow solid, m.p. 71°–83° C. Two recrystallizations from cyclohexane gives 3.43 grams of product, m.p. 87°–89° C.

EXAMPLE 8

Compound No. 15

5,5-Dimethyl-2-(3-morpholinylidene)-1,3-cyclohexanedione

A mixture of 3-ethoxy-3,4-dehydromorpholine (10.23 grams, 0.08 mole) and dimedone (11.1 grams, 0.08 mole) is heated at 110°–117° C. for a 3.47-hour period. The solid residue is dissolved in methylene chloride and the organic solution extracted with four portions of 3N NaOH and then four times with 3N HCl. Partial neutralization of the acid solution with 3N NaOH causes precipitation of pure product, m.p. 175°–176° C., as a white solid, weight 3.39 grams after water-washing and vacuum drying. The methylene chloride phase is then dried over magnesium sulfate and stripped to give 10.37 grams of pale yellow solid product, m.p. 174°–176° C., for a total yield of 76.9%. Recrystallization of the second fraction of material from toluene gives an analytical sample, m.p. 176°–177° C.

In a manner similar to that employed in the above examples, other 1,3-diones and derivatives of this invention were prepared. Table I below sets forth the structures of the compounds prepared and Table II below indicates the physical properties and elemental analysis of said compounds.

TABLE I

Compounds Tested

| Compound No. | Y | $R^1$ | $R^2$ | $R^3$ | n. | X |
|---|---|---|---|---|---|---|
| 1 | —CH(CH$_3$)— | H | CH$_3$ | CH$_3$ | 1 | —CH$_2$— |
| 2 | —CH(CH$_3$)— | H | CH$_3$ | CH$_3$ | 0 | —CH$_2$— |
| 3 | —CH$_2$— | CH$_3$ | CH$_3$ | CH$_3$ | 0 | —CH$_2$— |
| 4 | —CH$_2$— | H | C(CH$_3$)$_3$ | H | 1 | —CH$_2$— |
| 5 | —CH$_2$— | H | CH(C$_2$H$_5$)$_2$ | H | 1 | —CH$_2$— |
| 6 | —CH$_2$— | H | (thiacyclohexyl) | | 1 | —CH$_2$— |
| 7 | —CH$_2$— | H | —CH(CH$_3$)$_2$ | H | 0 | —CH$_2$— |
| 8 | —CH$_2$— | CH$_3$ | CH$_3$ | CH$_3$ | 1 | —CH$_2$— |
| 9 | —CH$_2$— | H | —CH(CH$_3$)$_2$ | H | 1 | —CH$_2$— |
| 10 | —CH$_2$— | H | —CH(CH$_3$)$_2$ | H | 0 | —NH— |
| 11 | —CH$_2$— | H | CH$_3$ | CH$_3$ | 1 | —NH— |
| 12 | —CH$_2$— | H | —CH(CH$_3$)$_2$ | H | 1 | —NH— |
| 13 | —CH(CH$_3$)— | H | —CH(CH$_3$)$_2$ | H | 1 | —NH— |
| 14 | —CH(CH$_3$)— | H | CH$_3$ | CH$_3$ | 1 | —NH— |
| 15 | O | H | CH$_3$ | CH$_3$ | 1 | —CH$_2$— |
| 16 | —CH$_2$— | H | CH$_3$ | CH$_3$ | 0 | —CH$_2$— |
| 17 | —CH$_2$— | H | CH$_3$ | CH$_3$ | 1 | —CH$_2$— |
| 18 | —CH$_2$— | H | CH$_3$ | CH$_3$ | 2 | —CH$_2$— |
| 19 | —CH$_2$— | H | CH$_3$ | CH$_3$ | 0 | —NH— |

TABLE II

PHYSICAL PROPERTIES AND ELEMENTAL ANALYSES OF NOVEL COMPOUNDS

| Compound No. | Mp °C. | Molecular Formula | Calculated | | | Found | | |
|---|---|---|---|---|---|---|---|---|
| | | | C | H | N | C | H | N |
| 1 | 174 | C$_{14}$H$_{21}$NO$_2$ | 71.45 | 8.99 | 5.95 | 71.64 | 9.18 | 5.84 |

TABLE II-continued
PHYSICAL PROPERTIES AND ELEMENTAL ANALYSES OF NOVEL COMPOUNDS

| Compound No. | Mp °C. | Molecular Formula | Calculated C | Calculated H | Calculated N | Found C | Found H | Found N |
|---|---|---|---|---|---|---|---|---|
| 9 | 85–87 | $C_{14}H_{21}NO_2$ | 71.45 | 8.99 | 5.95 | 71.89 | 8.91 | 5.96 |
| 7 | 143.5–145 | $C_{13}H_{19}NO_2$ | 70.56 | 8.65 | 6.33 | 70.31 | 8.70 | 6.50 |
| 8 | 94.5–96 | $C_{14}H_{21}NO_2$ | 71.45 | 8.99 | 5.95 | 71.55 | 9.01 | 6.02 |
| 10 | 223–225 | $C_{12}H_{18}N_2O_2$ | 64.84 | 8.16 | 12.60 | 64.57 | 8.46 | 12.45 |
| 11 | 197–199 | $C_{12}H_{18}N_2O_2$ | 64.84 | 8.16 | — | 64.76 | 8.18 | — |
| 12 | 144–146 | $C_{13}H_{20}N_2O_2$ | 66.07 | 8.53 | 11.86 | 66.48 | 8.52 | 11.80 |
| 14 | 164–165 | $C_{13}H_{20}N_2O_2$ | 66.07 | 8.53 | 11.86 | 66.24 | 8.81 | 11.78 |
| 13 | 87–89 | $C_{14}H_{22}N_2O_2$ | 67.16 | 8.86 | 11.19 | 66.66 | 8.74 | 11.46 |
| 15 | 175–176 | $C_{12}H_{17}NO_3$ | 64.55 | 7.67 | 6.27 | 64.32 | 7.72 | 6.24 |
| 2 | 152–153 | $C_{13}H_{19}NO_2$ | 70.56 | 8.65 | 6.33 | 70.64 | 8.78 | 6.25 |
| 3 | 150–151 | $C_{13}H_{19}NO_2$ | 70.56 | 8.65 | 6.33 | 70.79 | 8.52 | 6.34 |
| 4 | 86–87 | $C_{15}H_{23}NO_2$ | 72.25 | 9.30 | 5.61 | 71.98 | 9.30 | 5.65 |
| 5 | 73.5–76.5 | $C_{16}H_{25}NO_2$ | 72.96 | 9.57 | 5.32 | 73.17 | 9.61 | 5.27 |
| 6 | 182.5–183.5 | $C_{16}H_{23}NO_2$ | 73.53 | 8.87 | 5.36 | 73.33 | 8.57 | 5.35 |

The compounds of this invention possess activity both as pre-emergence and post-emergence herbicides and, accordingly, one aspect of this invention comprises the application of the operative materials to undesired vegetation by any means whereby said materials are brought into contact with living plants (which include seeds and germinating seedlings), e.g., by application to the soil before any plants emerge or by direct application to foliage.

The compounds are effective for both grassy weeds such as crabgrass, wild oats, barnyard grass, giant foxtail, green foxtail, quackgrass, and rye grass, and broadleaf weeds such as mustard, pigweed, velvetleaf, and black nightshade which are readily controlled while a number of crops are unaffected.

The toxicants may be applied conveniently in the form of a spray containing the active ingredient in a concentration within the range of 0.01–20.0% by weight, and preferably from 1 to 10.0% by weight. Thorough coverage of the foliage is effected for contact killing. For pre-emergence control of plants amounts within the range of 1/16 to 100 pounds per acre are generally used.

The compounds may be dispersed directly in water or a solution in an organic solvent, such as acetone, dimethylformamide, and dimethylsulfoxide emulsified in aqueous medium by the aid of a dispersing agent. As dispersing and wetting agents there may be employed soft or hard sodium or potassium soaps, alkylated aromatic sodium sulfonates such as sodium dodecylbenzenesulfonate, an amine salt, as for example dibutylammonium dodecylbenzenesulfonate, alkali metal salts of sulfated fatty alcohols, ethylene oxide condensation products of alkyl phenols, or tall oil or higher mercaptans and other dispersing and wetting agents. Formulation of dry compositions is accomplished by mixing with finely divided solid carriers. Suitable carriers comprise talc, clay, pyrophyllite, silica and fuller's earth. Usually the toxicant will be only a minor proportion. The dry formulation may be used as a dust or dispersed in aqueous medium before application. If the latter, it is convenient to incorporate a wetting or dispersing aid into the formulation.

Both the solid and the liquid formulations above described are useful in the application of herbicides because they facilitate uniform distribution and aid in the destruction of undesirable plants by maintaining the active ingredient in a form which enables prompt assimilation by the plant and efficient utilization of its weed destroying properties. The described conditioning agents enable the proper use by an unskilled operator without elaborate equipment to achieve the desired herbicidal effects.

The effectiveness of compounds representative of this invention as terrestrial herbicides were evaluated as pre-emergence herbicides and post-emergence herbicides. The test plants were mustard, teaweed, velvetleaf and giant foxtail. For the pre-emergence test, seeds of the type of plants as shown in Table III were sown in fresh soil. In the pre-emergence test, the soil was sprayed with a solution of the test compound immediately after the seeds were planted. The solution was about a 1% by weight solution of the test compound in acetone. The compounds were applied at the rate of 8 lbs/acre of soil surface, except where otherwise indicated in Table III.

Approximately three weeks after spray applications, the herbicidal activity of the compound was determined by visual observation of the treated areas in comparison with untreated controls. These observations are reported in Table III as percent control of plant growth.

In the post-emergence test the soil and developing plants were sprayed about two weeks after the seeds were sown. Except where indicated otherwise in Table III, the compounds were applied at the rate of 1 lb/acre from about a 1% by weight solution of the test compound in acetone. The post-emergence herbicidal activity was measured in the same way as the pre-emergence activity at three weeks following treatment.

The results are indicated in Table III below:

TABLE III
HERBICIDAL ACTIVITY AT 1 LB/ACRE
% CONTROL OF TEST PLANT INDICATED

| Compound No. | Mustard Post | Mustard Pre | Teaweed Post | Teaweed Pre | Velvetleaf Post | Velvetleaf Pre | Giant Foxtail Post | Giant Foxtail Pre |
|---|---|---|---|---|---|---|---|---|
| 16 | 26 | 40 | 14 | — | 30 | — | 0 | 36 |
| 17 | 0 | (100)[a] | 50 | 0 | 32 | 32 | 16 | 77 |
| 18 | (59)[a] | (100)[a] | (100)[a] | (62)[a] | (20)[a] | (100)[a] | 0 | (14)[a] |

TABLE III-continued

| | HERBICIDAL ACTIVITY AT 1 LB/ACRE % CONTROL OF TEST PLANT INDICATED | | | | | | | |
|---|---|---|---|---|---|---|---|---|
| | Mustard | | Teaweed | | Velvetleaf | | Giant Foxtail | |
| Compound No. | Post | Pre | Post | Pre | Post | Pre | Post | Pre |
| 19 | 40 | 100 | 14 | 74 | 35 | 88 | 0 | 3 |
| 1 | 100 | 100 | 100 | 95 | 100 | 100 | 7 | 31 |
| 9 | 72 | 94 | 53 | 0 | 86 | 2 | 88 | 12 |
| 7 | 100 | 100 | 33 | 0 | 100 | 10 | 2 | 14 |
| 8 | 82 | 100 | 46 | — | 65 | — | 19 | 53 |
| 10 | 84 | 100 | 72 | 100 | 14 | 100 | 0 | 0 |
| 11 | 100 | 100 | 100 | 83 | 100 | 100 | 14 | 86 |
| 12 | 75 | 100 | 59 | 76 | 100 | 100 | 32 | 2 |
| 14 | 100 | 100 | 100 | 100 | 100 | — | 100 | 82 |
| 13 | 100 | 100 | 10 | 100 | 100 | — | 74 | 98 |
| 15 | 65 | 100 | 100 | 35 | 75 | 100 | 0 | 0 |
| 2 | $(82)^{(a)}$ | $(98)^{(a)}$ | $(53)^{(a)}$ | $(53)^{(a)}$ | $(37)^{(a)}$ | $(98)^{(a)}$ | 0 | $(12)^{(a)}$ |
| 3 | 22 | 62 | 6 | 0 | 12 | 20 | 0 | 6 |
| 4 | — | — | $[85]^{(b)}$ | 0 | $[100]^{(b)}$ | 0 | $[54]^{(b)}$ | $[30]^{(b)}$ |
| 5 | — | — | $[77]^{(b)}$ | — | $[76]^{(b)}$ | — | $[54]^{(b)}$ | — |
| 6 | Not tested below 8 lbs/acre | | | | | | | |
| 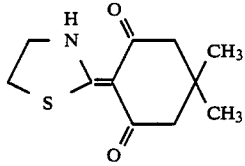 | $(68)^{(a)}$ | $(100)^{(a)}$ | $(100)^{(a)}$ | $(97)^{(a)}$ | $(0)^{(a)}$ | $(100)^{(a)}$ | $(10)^{(a)}$ | $(22)^{(a)}$ |

Prior Art Compound
Sankyo: Japan 73,1097

$^{(a)}$Tested at 2 lbs/acre
$^{(b)}$Tested at 4 lbs/acre

It will be understood that the plant species employed in the above tests are merely representative of a wide variety of plants that can be controlled by the use of the compounds of this invention.

Table IV below is illustrative of the cotton defoliant use that can be realized via the application of certain of the compositions of this invention.

TABLE IV

| COTTON DEFOLIANT EVALUATION | | |
|---|---|---|
| Compound No. | Rate lbs/acre | % Leaf Abcission |
| 4 | 5 | 10 |
| 1 | 5 | 10 |
| 16 | 5 | 5 |

Although the invention has been illustrated by the preceding examples it is not to be construed as being limited to the materials employed therein, but rather, the invention is directed to the generic area as hereinbefore disclosed. Various modifications and embodiments thereof can be made without departing from the spirit and scope thereof.

I claim:

1. A herbicidal composition comprising an acceptable carrier and an active toxicant wherein said toxicant comprises a herbicidally effective amount of a compound of the formula:

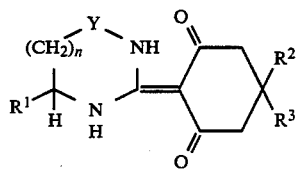

wherein:

Y is $CH_2$ or $CHR^4$; wherein $R^4$ is $C_1$-$C_3$ alkyl $R^1$ is hydrogen or $C_1$-$C_3$ alkyl, with the proviso that the number of carbon atoms in $R^1$ plus Y is less than or equal to 5;

$R^2$ is hydrogen or $C_1$-$C_5$ straight chain, branches or cyclic alkyl;

$R^3$ is $C_1$-$C_3$ straight chain alkyl or $R^2$ and $R^3$ together may form a cyclopentane or cyclohexane ring wherein the number of carbon atoms in $R^2$ plus $R^3$ is less than or equal to 6; and n is b 0, 1, or 2.

2. A herbicidal composition comprising an acceptable carrier and as the active toxicant, a herbicidally effective amount of 5-(1-methylethyl)-2-(2-imidazolidinylidene)-1,3-cyclohexanedione.

3. A herbicidal composition comprising an acceptable carrier and as the active toxicant, a herbicidally effective amount of 5,5-dimethyl-2-(2-hexahydropyrimidinylidene)-1,3-cyclohexanedione.

4. A herbicidal composition comprising an acceptable carrier and as the active toxicant, a herbicidally effective amount of 5(1-methylethyl)-2-(2-hexahydropyrimidinylidene)-1,3-cyclohexanedione.

5. A herbicidal composition comprising an acceptable carrier and as the active toxicant, a herbicidally effective amount of 5,5-dimethyl-2-(4-methyl-2-hexahydropyrimidinylidene)-1,3-cyclohexanedione.

6. A herbicidal composition comprising an acceptable carrier and as the active toxicant, a herbicidally effective amount of 5-(1-methylethyl)-2-(4-methyl-2-hexahydropyrimidinylidine)-1,3-cyclohexanedione.

7. A method of controlling undesired plant growth which comprises subjecting said plant to a herbically effective amount of the compound of the formula:

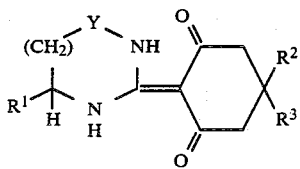

wherein:
Y is $CH_2$ or $CHR^4$, wherein $R^4$ is $C_1$–$C_3$ alkyl
$R^1$ is hydrogen or $C_1$–$C_3$ alkyl, with the proviso that the number of carbon atoms in $R^1$ plus Y is less than or equal to 5;
$R^2$ is hydrogen or $C_1$–$C_5$ straight chain, branches or cyclic alkyl;
$R^3$ is $C_1$–$C_3$ straight chain alkyl or $R^2$ and $R^3$ together may form a cyclopentane or cyclohexane ring wherein the number of carbon atoms in $R^2$ plus $R^3$ is less than or equal to 6; and n is 0, 1, or 2.

8. A method of controlling undesired plant growth which comprises subjecting said plant to a herbicidally effective amount of 5-(1-methylethyl)-2-(2-imidazolidinylidene)-1,3-cyclohexanedione.

9. A method of controlling undesired plant growth which comprises subjecting said plant to a herbicidally effective amount of 5,5-dimethyl-2-(2-hexahydropyrimidinylidene)-1,3-cyclohexanedione.

10. A method of controlling undesired plant growth which comprises subjecting said plant to a herbicidally effective amount of 5-(1-methylethyl)-2-(2-hexahydropyrimidinylidene)-1,3-cyclohexanedione.

11. A method of controlling undesired plant growth which comprises subjecting said plant to a herbicidally effective amount of 5,5dimethyl-2-(4-methyl-2-hexahydropyrimidinylidene)-1,3-cyclohexanedione.

12. A method of controlling undesired plant growth which comprises subjecting said plant to a herbicidally effective amount of 5-(1-methylethyl)-2-(4-methyl-2-hexahydropyrimidinylidine)-1,3-cyclohexanedione.

* * * * *